United States Patent [19]

Thiem et al.

[11] Patent Number: 4,659,810

[45] Date of Patent: Apr. 21, 1987

[54] PROCESS FOR THE PREPARATION OF 1-AZIDOALDOSES

[75] Inventors: Joachim Thiem, Münster; Hans-Matthias Deger, Hofheim am Taunus; Cenek Kolar, Marburg; Matthias Kreuzer, Münster, all of Fed. Rep. of Germany

[73] Assignee: Hoechst Aktiengesellschaft, Fed. Rep. of Germany

[21] Appl. No.: 749,752

[22] Filed: Jun. 28, 1985

[30] Foreign Application Priority Data

Jun. 30, 1984 [DE] Fed. Rep. of Germany ....... 3424183
Feb. 2, 1985 [DE] Fed. Rep. of Germany ....... 3503620

[51] Int. Cl.$^4$ .............................................. C07H 1/00
[52] U.S. Cl. ......................................... 536/22; 536/55; 536/124; 536/55.3
[58] Field of Search .......................... 536/22, 55, 55.3

[56] References Cited

U.S. PATENT DOCUMENTS 4,220,643 9/1980 Suami ..................................... 536/22

OTHER PUBLICATIONS

F. Micheel et al., Chem. Bev., 90, 1595 (1957).
A. Bertho, Che. Bev., 63, 841 (1930).
A. Bertho and D. Aures, Liebigs Ann. Chem., 592, 54 (1955).
Micheel, "Chem. Ber.", vol. 88, No. 4, 1955, pp. 475–479.

*Primary Examiner*—Johnnie R. Brown
*Attorney, Agent, or Firm*—Finnegan, Henderson, Farabow, Garrett & Dunner

[57] ABSTRACT

1-Azidoaldoses are obtained by reacting 1-fluoroaldoses with metal azides in polar, water-miscible, preferably water-containing, solvents. The hydroxyl groups do not react at the same time, so that they need not be protected or can be present in a derivatized form.

17 Claims, No Drawings

PROCESS FOR THE PREPARATION OF 1-AZIDOALDOSES

Both classical and modern synthetic carbohydrate chemistry depends on the broad use of expensive protective group techniques, which are unavoidable in some cases for carrying out selective reactions on a polyfunctional sugar molecule but in some cases for stabilizing compounds which in the unprotected state are labile. The high expenditure of chemicals, time and work entailed greatly restricts the broad industrial use of carbohydrate derivatives.

For example, β-1-azidoaldoses, which are intermediates in the synthesis of, for instance, 1,6-anhydro-sugars (F. Micheel et al., Chem. Ber. 88, 475 (1955) and 88, 479 (1955)) and triazolyl-N-glycosides (F. Micheel et al., Chem. Ber. 90, 1595 (1957)) can only be obtained from aldoses via a four-stage synthesis (R. U. Lemieux in Meth. Carbohydr. Chem. II, page 221, Academic Press 1963, and A. Bertho, Chem. Ber. 63, 841 (1930)). The azide group is introduced by reaction of tetraacetyl-α-glycosyl bromide with sodium azide, in the absence of water, to give tetraacetyl-β-glycosyl azide, from which the free β-azidoaldoses can be prepared by removal of the acetyl groups (A. Bertho, Loc. cit.).

We have now found, surprisingly, that 1-azidoaldoses can be prepared directly, i.e. without use of intermediates carrying protective groups, by reacting unprotected 1-fluoroaldoses with metal azides in the presence of a polar water-miscible organic solvent. In this reaction, the azidoaldoses are formed with configuration inversion or configuration retention. The hydroxyl groups do not react at the same time, and accordingly they need not be protected or can be present in a derivatized form.

The addition of water to the reaction mixture in general substantially increases the reaction velocity.

Suitable starting materials are, from the series of the pentoses, the α- or β-1-fluoroaldoses, such as α- or β-1-fluoroxylose, -arabinose or -ribose, from the series of the hexoses, for example, α- or β-1-fluoroglucose, -galactose, -mannose, -gulose or -altrose, and from the series of the disaccharides, for example, α- or β-1-fluoro-maltose, -cellobiose, -lactose, -isomaltose or -gentiobiose, but also derivatives of these sugars, such as, for example, α- or β-1-fluoro-N-acetyl-2-amino-2-desoxy-glucose.

Suitable metal azides are all water-soluble azides, preferably the alkaline earth metal azides, such as calcium azide, and the alkali metal azides, such as sodium azide and potassium azide. The alkaline earth metal azides can be used in the reaction as such, but also in the nascent state, for example as produced from sodium azide and calcium chloride. Since a stoichiometric reaction is involved, the metal azide is employed at least in the stoichiometric amount, but in most cases in an excess corresponding to the practical conditions. The preferred amount is between a 50% excess and three times the stoichiometrically required amount.

Suitable water-miscible organic solvents are polar protic and aprotic solvents, for example lower alkanols such as methanol, ethanol, propanol and isopropanol, acetonitrile, amides such as formamide, dimethylformamide or N-methylpyrrolidone, as well as ethers such as monomethoxyethane or dimethoxyethane, monoethoxyethane or tetrahydrofuran.

The reaction is advantageously carried out at temperatures from 0° C. upward, at room temperature or elevated temperature, preferably at 40°–120° C., in particular at 60°–100° C., especially if alkali metal azides are used. The reaction with alkaline earth metal azides, especially calcium azide, can with advantage be carried out even at the lower temperatures, from 0° C. upwards, but is preferably carried out at from room temperature to 60° C. If low-boiling organic solvents are used, the reaction can be carried out under pressure, namely, for example, in a closed vessel; preferably, however, the upper temperature limit chosen is the boiling point of the reaction system, which thus means that in practice it is advantageous to work under reflux. The salts formed can be isolated in the usual manner. Advantageously, they are separated off with the aid of an ion exchanger or by means of a molecular sieve, in water or in mixtures of water with the abovementioned water-miscible organic solvents.

The examples which follow explain in more detail advantageous embodiments of the invention.

EXAMPLES (1) Preparation of β-D-glucopyranosyl azide=compound 1

9.1 g of α-D-glucosyl fluoride were heated with 3.57 g of sodium azide in a mixture of 50 ml of methanol and 10 ml of water for 48 hours under reflux. The methanol was then evaporated off and the residue was taken up in 50 ml of water and desalinated by means of an ion exchanger. The water was evaporated off under the vacuum from a water pump and the oily residue was dehydrated by distillation with ethanol. The syrup thus obtained was freed from residual ethanol by heating at 50° C. in a high vacuum. 9.7 g of a pale yellow syrup were obtained; according to analysis (gas chromatography), this contained 92% of β-1-azidoglucose.

If the analogous procedure was followed except that water was excluded, β-1-azidoglucose was only detectable in small amounts (after the same reaction time).

(2) Preparation of β-D-glucopyranosyl azide=compound 1

9.1 g of β-D-glucosyl fluoride were stirred with 3.57 g of sodium azide in a mixture of 50 ml of acetonitrile and 10 ml of water for 24 hours at 70° C. After the mixture had been worked up as in Example 1, 9.0 g of a syrup were obtained, consisting of 78% of β-D-azidoglucose and 6% of D-glucose.

(3) Preparation of β-D-galactopyranosyl azide=compound 2

9.1 g of α-D-galactosyl fluoride were heated with 3.57 g of sodium azide in a mixture of 50 ml of methanol and 10 ml of water for 24 hours under reflux. After the mixture had been worked up as in Example 1, 9.6 g of a syrup, containing 94% of β-D-azidogalactose, were obtained. Acetylation and recrystallization from isopropanol gave 13.2 g (71% of theory) of tetraacetyl-β-D-azidogalactose, of melting point 101°–103° C.

(4) Preparation of β-cellobiosyl azide=compound 3

6.9 g of α-cellobiosyl fluoride were stirred with 1.42 g of sodium azide in a mixture of 70 ml of ethanol and 15 ml of water for 72 hours at 60° C. After the mixture had been worked up as in Example 1, 9.6 g of a syrup containing 85% of β-azidocellobiose were obtained.

(5) Preparation of α-D-mannopyranosyl azide=compound 4

12 g of α-mannosyl fluoride were heated with 4.7 g of sodium azide in 100 ml of acetonitrile for 80 hours at the reflux temperature. After the mixture had been worked up as in Example 1, 10.3 g of a syrup containing 92% of α-azidomannose were obtained.

(6) Preparation of compound 1

94.9 g (0.855 mole) of calcium chloride and 129.7 g (1.995 moles) of sodium azide were suspended in 800 ml of 95% strength aqueous methanol. After 30 minutes stirring at room temperature, the suspension, which now contained calcium azide, was treated in situ with 55.4 g (0.285 mole) of α-D-glucopyranosyl fluoride dissolved in 200 ml of methanol. The suspension was then stirred for 15 hours at room temperature, the course of the reaction being followed by thin layer chromatography (migrating agent: chloroform/methanol, 3:1). After completion of the reaction, the suspension was filtered off and the residue was rinsed with ethanol. The combined filtrates were evaporated under a vacuum from a water pump. The resulting syrup was dissolved in ethanol, the solution was filtered over a 4 A molecular sieve, and the filtrate was concentrated under the vacuum from a water pump, to give a syrup. Yield: 54 g (92.3%); IR: 2115 cm$^{-1}$ (—N$_3$).

The β-glucopyranosyl azide was shown to be present as 2,3,4,6-tetra-O-acetyl-β-D-glucopyranosyl azide by NMR spectroscopy and by polarimetry ($[\alpha]^{20}= -32°$ c=1 in chloroform; literature value $[\alpha]^{20}= -33°$ c=2.48 in chloroform according to A. Bertho and D. Aures, Liebigs Ann. Chem. 592, 54 (1955)).

(7) The following 1-azidoaldoses were prepared as described in Example 6 and characterized by IR and NMR spectroscopy, as their peracetates:

β-D-Galactopyranosyl azide: (compound 2),
β-Cellobiosyl azide: (compound 3),
α-D-Mannopyranosyl azide: (compound 4).

We claim:

1. The process for the manufacture of 1-azidoaldoses which comprises reacting a 1-fluoro-aldose with a metal azide in the presence of a polar, water-miscible solvent.

2. A process as claimed in claim 1, wherein the reaction is carried out at a temperature in the range from 0° C. to the boiling point of the reaction system.

3. A process as claimed in claim 2, wherein the reaction is carried out at a temperature in the range from 40° to 120° C.

4. A process as claimed in claim 3, wherein the reaction is carried out at a temperature in the range from 60° to 100° C.

5. A process as claimed in claim 3, wherein the metal azide is an alkali azide.

6. A process as claimed in claim 1, wherein the reaction is carried out at a temperature in the range from 0° C. to 60° C. and the metal azide is an alkaline earth metal azide.

7. A process as claimed in claim 1, wherein the polar water-miscible solvent is a lower alkanol, acetonitrile, an amide or an ether.

8. A process as claimed in claim 1, wherein the reaction mixture also contains water.

9. A process as claimed in claim 1, wherein the salts generated are removed from the reaction mixture by means of an ion exchanger.

10. A process as claimed in claim 1, wherein the salts generated are removed from the reaction mixture by means of a molecular sieve in water or a mixture thereof with at least one water-miscible organic solvent.

11. A process as claimed in claim 1, wherein the metal azide is an alkaline earth metal azide or an alkali metal azide.

12. A process as claimed in claim 11, wherein the metal azide is sodium azide, potassium azide or calcium azide.

13. A process as claimed in claim 12, wherein the metal azide is calcium azide and the reaction is carried out at a temperature in the range from ambient temperature to 60° C.

14. A process as claimed in claim 1, wherein the alkaline earth metal azide is reacted in statu nascendi.

15. A process as claimed in claim 1, wherein the metal azide is applied at least in the stoechiometric amount and at most in triple amount of the stoechiometric amount.

16. A process as claimed in claim 1, wherein the 1-fluoro-aldose is unprotected.

17. A process as claimed in claim 1, wherein the 1-azidoaldoses are prepared directly and without the use of intermediates carrying protective groups.

* * * * *